(12) United States Patent
Bartko

(10) Patent No.: US 8,441,632 B2
(45) Date of Patent: May 14, 2013

(54) BIOLOGICAL AND CHEMICAL MICROSCOPIC TARGETING

(75) Inventor: Andrew P. Bartko, Columbus, OH (US)

(73) Assignee: Battelle Memorial Institute, Columbus, OH (US)

( * ) Notice: Subject to any disclaimer, the term of this patent is extended or adjusted under 35 U.S.C. 154(b) by 276 days.

(21) Appl. No.: 12/868,553

(22) Filed: Aug. 25, 2010

(65) Prior Publication Data
US 2011/0026018 A1  Feb. 3, 2011

Related U.S. Application Data

(63) Continuation of application No. PCT/US2009/035316, filed on Feb. 26, 2009.

(60) Provisional application No. 61/031,517, filed on Feb. 26, 2008.

(51) Int. Cl.
*G01J 3/44* (2006.01)
*G01N 21/65* (2006.01)

(52) U.S. Cl.
USPC .......................................................... 356/301

(58) Field of Classification Search ................... 356/301, 356/417
See application file for complete search history.

(56) References Cited

U.S. PATENT DOCUMENTS

| 5,048,959 A | | 9/1991 | Morris et al. | |
|---|---|---|---|---|
| 5,623,342 A | * | 4/1997 | Baldwin et al. | ............... 356/301 |
| 5,822,061 A | | 10/1998 | Delhaye et al. | |
| 7,057,721 B2 | * | 6/2006 | Gardner et al. | ............... 356/301 |
| 7,333,190 B1 | | 2/2008 | Pendell-Jones et al. | |
| 7,561,264 B2 | * | 7/2009 | Treado et al. | ................. 356/301 |
| 2005/0185178 A1 | | 8/2005 | Gardner, Jr. et al. | |
| 2007/0076208 A1 | | 4/2007 | Koo | |

FOREIGN PATENT DOCUMENTS

| EP | 0543578 A1 | 11/1992 |
|---|---|---|
| EP | 0543578 A1 | 5/1993 |
| WO | 96/10737 A1 | 4/1996 |
| WO | 9610737 A1 | 4/1996 |

OTHER PUBLICATIONS

International Preliminary Report on Patentability for PCT Application No. PCT/US2009/035316; Mailing Date of Sep. 10, 2010; The International Bureau of WIPO; Geneva, Switzerland.
Written Opinion of the International Searching Authority for PCT Application No. PCT/US2009/035316; Mailing Date of Sep. 10, 2010; European Patent Office; Munich, Germany.
EPO ISA, International Search Report and Written Opinion, Jun. 19, 2009.

* cited by examiner

*Primary Examiner* — Layla Lauchman
(74) *Attorney, Agent, or Firm* — Thomas E. Lees, LLC

(57) ABSTRACT

Biological and chemical materials often contain many molecular bonds that connect carbon (C) hydrogen (H) atoms. These bonds covalently share electrons that can be optically activated by light. The incident light interaction with the C—H molecular bond spectrally shifts of the incident light proportional to the vibrational, or more precisely polarizability, constant of the electrons that bind the C—H atoms. This process is called Raman scattering. For C—H, C—$H_2$ and C—$H_3$ bonding schemes, the spectral shift is approximately 3000 $cm^{-1}$ lower in energy from the incident light energy. Using this fundamental spectral shift coupled with optical microscopy, the ability to detect materials that possess C—$H_x$ (where x=1, 2 or 3) is possible.

22 Claims, 3 Drawing Sheets

BIOLOGICAL AND CHEMICAL MICROSCOPIC TARGETING

CROSS REFERENCE TO RELATED APPLICATIONS

This application is a continuation of International Application No. PCT/US2009/035316, filed Feb. 26, 2009, entitled "BIOLOGICAL AND CHEMICAL MICROSCOPIC TARGETING", which claims the benefit of U.S. Provisional Patent Application Ser. No. 61/031,517, filed Feb. 26, 2008, entitled "BIOLOGICAL AND CHEMICAL MICROSCOPIC TARGETING", the disclosures of which are hereby incorporated by reference.

BACKGROUND

The present invention relates in general to biological and chemical microscopic targeting.

The monitoring of atmospheric particulate matter (PM) such as airborne bioaerosols has received an increasing amount of attention in recent years because of the potential impact of particulates on climatic processes, on human health and because of the role particles play in atmospheric transport and deposition of pollutants. For example, it may be desirable to analyze the air in a predetermined location for particulates that fall within a range of sizes that can be inhaled, such as naturally occurring or artificially produced airborne pathogens, allergens, bacteria, viruses, fungi and biological or chemical agents that are found in or are otherwise introduced into the location.

As another example, it may be desirable to detect the presence of particular airborne particulates in semiconductor clean rooms, pharmaceutical production facilities and biotechnology laboratories to verify that there has been no contamination produced in such environments that would create undesirable environmental exposures or adversely affect manufacturing, testing or experimental processes. Similarly, the ability to detect the presence of particular airborne particulates in hospitals, nursing homes, rehabilitation centers and other care facilities may be beneficial to assist in preventing the spread of disease, infection or harmful bacteria.

The monitoring of atmospheric particulate matter further finds application for assessments of human health risk, environmental contamination and for compliance with National Air Quality Standards (NAAQS), e.g., to monitor the air in public and commercial building air purification and distribution systems, work sites such as mines, sewage facilities, agricultural and manufacturing facilities, outside areas such as street corners, flues and smokestacks and other locations where it is desirable to monitor environmental hygiene, such as residences exposed to microorganisms, plants or animals.

BRIEF SUMMARY

According to aspects of the present invention, a biological and chemical microscopic targeting system comprises a light source configured to emit a laser beam and an imaging system configured to direct the beam towards a sample substrate along at least one optical path such that beam divergence causes the laser spot to be defocused with respect to an optical focal plane of the imaging system. The imaging system comprises an objective lens wherein the beam passes through the objective lens to illuminate the sample substrate and light collected from the sample substrate is directed back through the objective lens. The system further comprises optics that separate inelastically scattered photons from elastic incident photons. The optics comprise at least one filter that filters the scattered photons for spectrally shifted wavelengths due to material on the sample substrate whose $C-H_x$ molecular bonds inelastically shift the wavelength of the incident photons. Still further, the system comprises an output device that receives the filtered photons to output information that discriminates between at least one biological particle of interest that possesses $C-H_x$, from non biological particles contained on the sample substrate, to a user.

According to still further aspects of the present invention, a method of performing biological and chemical microscopic targeting comprises directing a laser beam from a light source towards a sample substrate along at least one optical path of an imaging system such that beam divergence causes the laser spot to be defocused with respect to an optical focal plane of the imaging system, passing the beam through an objective lens to illuminate the sample substrate and collecting light from the sample substrate that reflects back through the imaging system. The method further comprises separating inelastically scattered photons from elastic incident photons, where the inelastically scattered photons are filtered for spectrally shifted wavelengths due to material on the sample substrate whose $C-H_x$ molecular bonds inelastically shift the wavelength of the incident photons and passing the filtered inelastically scattered photons to an output device to convey information that discriminates between at least one biological particle of interest that possesses $C-H_x$, from non biological particles contained on the sample substrate, to a user.

BRIEF DESCRIPTION OF THE SEVERAL VIEWS OF THE DRAWINGS

The following detailed description of various aspects of the present invention can be best understood when read in conjunction with the following drawings, where like structure is indicated with like reference numerals, and in which.

DETAILED DESCRIPTION

Biological and chemical materials often contain many molecular bonds that connect carbon (C) and hydrogen (H) atoms. These bonds covalently share electrons that can be optically activated by light. The incident light interaction with the C—H molecular bond spectrally shifts the incident light proportional to the vibrational, or more precisely polarizability, constant of the electrons that bind the C—H atoms. This process is called Raman scattering. For C—H, $C-H_2$ and $C-H_3$ bonding schemes, the spectral shift is approximately 3000 $cm^{-1}$ lower in energy from the incident light energy. According to various aspects of the present invention, this fundamental spectral shift, coupled with optical microscopy, is utilized to detect materials that possess $C-H_x$ (where x=1, 2 or 3).

Figure 1:
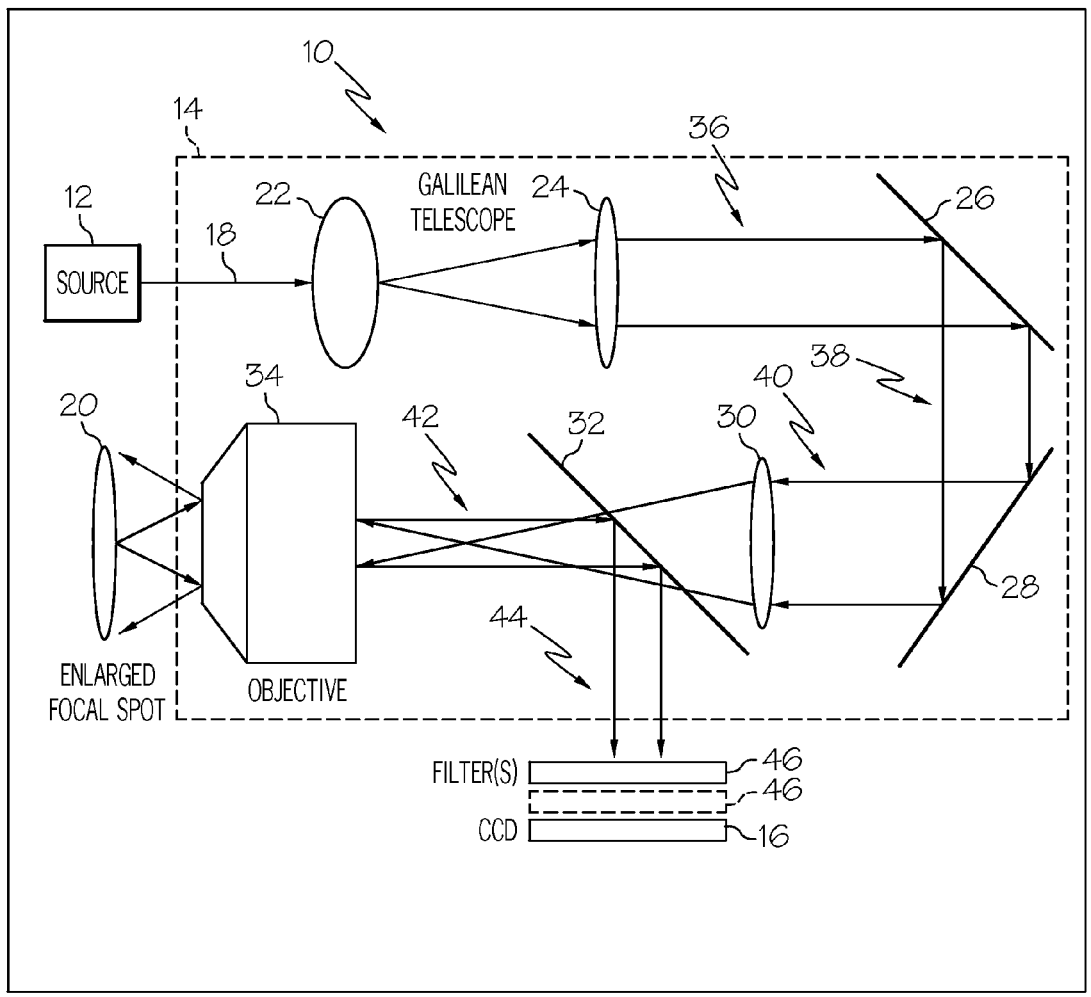
FIG. 1 is a schematic view of a system for targeting of biological and chemical materials according to various aspects of the present invention.

With reference generally to FIG. 1, targeting of biological and chemical materials can be accomplished according to various aspects of the present invention, using an optical imaging system 10. As illustrated, the optical imaging system 10 includes in general, a light source 12, optics 14 and at least one image output device 16.

The light source 12 may comprise, for example, a high intensity laser capable of generating a laser beam 18 having a narrow spectral bandwidth. The optics 14 direct the beam 18 towards a sample area 20 and light from the sample area 20 that is reflected back through the optics 14 is filtered and processed by the image output device 16, such as a charge coupled device (CCD). In this regard, the image output device 16 receives inelastically scattered photons to output information regarding the materials contained on the sample substrate to a user, as will be described in greater detail herein.

For example, as illustrated, the optics may comprise a first lens 22, a second lens 24, a first reflection surface 26, a second reflection surface 28, a third lens 30, a optical device 32 and an fourth lens 34. The beam 18 emitted from the light source 12 passes through the first lens 22 and travels through the second lens 24 along a first optical path 36. The beam 18 is then redirected approximately 90 degrees by the first reflection surface 26 and is directed along a second optical path 38 to the second reflection surface 28, which redirects the beam 18 by approximately another 90 degrees along a third optical path 40. As such, the third optical path 40 is generally parallel to, but not coaxial with the first optical path 36. Moreover, the beam 18 travels along the first optical path 36 in a direction generally opposite the direction of the beam 18 along the third optical bath 40.

The beam 18 travels along the third optical path 40 through the third lens 30, the optical device 32 and the fourth lens 34. In this regard, the fourth lens 34 serves as an objective to focus the beam 18 onto the sample area 20, which may comprise an area of a sample substrate that provides the sample to be analyzed. The beam 18 impinges upon the sample area 20 and is reflected from the sample area 20 back through the fourth lens (objective) 34 along a fourth optical path 42 that is generally opposite in direction of the third optical path 40. The light reflected back through the objective 34 is directed by the optical device 32 to the image output device 16.

Divergence in the optical system 14 causes the laser spot of the beam 18 to be defocused with respect to the optical focal plane (imaging plane) of the imaging system, which may occur in two or fewer dimensions normal to the optic axis, e.g., the image output device 16. When the sample area 20 of the sample substrate contains materials that possess C—$H_x$, incident photons will interact with the molecular bonds and inelastically (spectrally) shift the wavelength of the incident photons.

The inelastically scattered photons are collected by the imaging system, e.g., the image output device 16. For example, the light reflected back through the objective 34 travels along the fourth optical path 42 to the optical device 32. The optical device 32 redirects the light along the fourth optical path 42 along a fifth optical path 44. In this regard, the optical device 32 is transmissive to light traveling along the third optical path 40 from the third lens 30 towards the optical device 32. However, the optical device 32 is reflective of light traveling along the fourth optical path 42 from the objective 34 towards the optical device 32. In the exemplary arrangement, the third and fourth optical paths are coaxially aligned but in different directions. As such, the light traveling along the fourth optical path is illustrated with ray traces that are in a bolded line weight for distinction.

The inelastically scattered photons are separated from the elastic incident photons, e.g., using at least one appropriate filter device 46 and are passed to the image output device 16.

According to various aspects of the present invention, the utilization of a large laser spot or laser line enables a large amount of material to be examined within the field of view of the imaging system. In this regard, the first lens 22 and second lens 24 operate in the fashion of a Galilean telescope to expand the diameter of the laser beam 18. The laser beam 18 is then refocused by the third lens 30 with a focal length approximately equal to the distance between the lens and the back aperture of the microscope objective 34. However, other optics configurations may be implemented within the spirit and scope of the present invention.

For example, in an exemplary implementation, the laser source 12 emits a beam 18 comprising approximately 35 milliwatts of 632.8 nanometer (nm) laser radiation. The beam 18 passes through the optics 14, which are configured to provide an 80 micrometer$^2$($\mu m^2$) field to illuminate the sample area 20. The inelastically scattered photons from the sample area 20 are collected by the objective 34 and are reflected by the optical device 32, e.g., a long pass 633 nm dichroic mirror. The light reflected by the optical device 32 is filtered by the filter device 46, which may comprise for example, a 780 nm bandpass filter.

As yet another illustrative example, the laser source 12 may be configured to illuminate the sample area, such as in at least an 80 μm long line. Moreover, the laser source 12 may utilize less than 35 milliwatts of laser radiation having a wavelength, for example, between 576 nm and 650 nm. In this regard, the inelastically scattered photons are collected and are reflected by the optics 14, such as by a long pass dichroic mirror, a long pass filter and bandpass filter 3000 cm$^{-1}$ less than the laser wavelength.

The filtering provided by the long pass 633 nm dichroic mirror 32 and 780 nm bandpass filter 46 attenuates the fundamental wavelength of the laser beam 18 by approximately 8 orders of magnitude through the spectral range that is approximately 500 nm through 633 nm. Moreover, the bandpass filter 46 attenuates all light between 500 nm to 776 nm and also from 784 nm to 900 nm. However, in the 776 nm to 784 nm region, the filter 46 may transmit, for example, over 90% of the light.

According to various aspects of the present invention, the filter 46, e.g., the 780 nm bandpass filter, causes light in the transmitted wavelength range, e.g., 776 nm through 784 nm in the illustrative example, to be approximately 3000 cm$^{-1}$ lower in energy than the energy at the laser beam frequency. Thus, any material that contains C—$H_x$ molecular binding will inelastically scatter photons into this spectral region. Detection of these inelastic photons using an output device 16, such as a CCD camera, provides the ability to relate the spatial location of the identified material in a sample plane of the sample area 20.

The spatial C—$H_x$ inelastic scattering information may be utilized, for example, in concert with visible image spatial information, and/or other spatial information such as fluorescence spatial information to potentially increase the probability of the material being biological or chemical (organic) in nature.

According to various aspects of the present invention, other optical configurations may be implemented to address problems such as fluorescence. For instance, the filter 46 may be implemented using two filters to reduce the fluorescence content. As yet another example, two images, one taken with each filter 46, may be subtracted from one another to reveal the spectrally narrow region of the spectrum where C—$H_x$ inelastic scattering occurs and would significantly discount the fluorescence perturbation to the targeting methodology. Moreover, other types of molecular bonding such as nitrogen (N)-hydrogen (H) bonding are ubiquitous in biological materials and may also prove to increase the probability of spatially detecting materials of interest.

Figure 2:
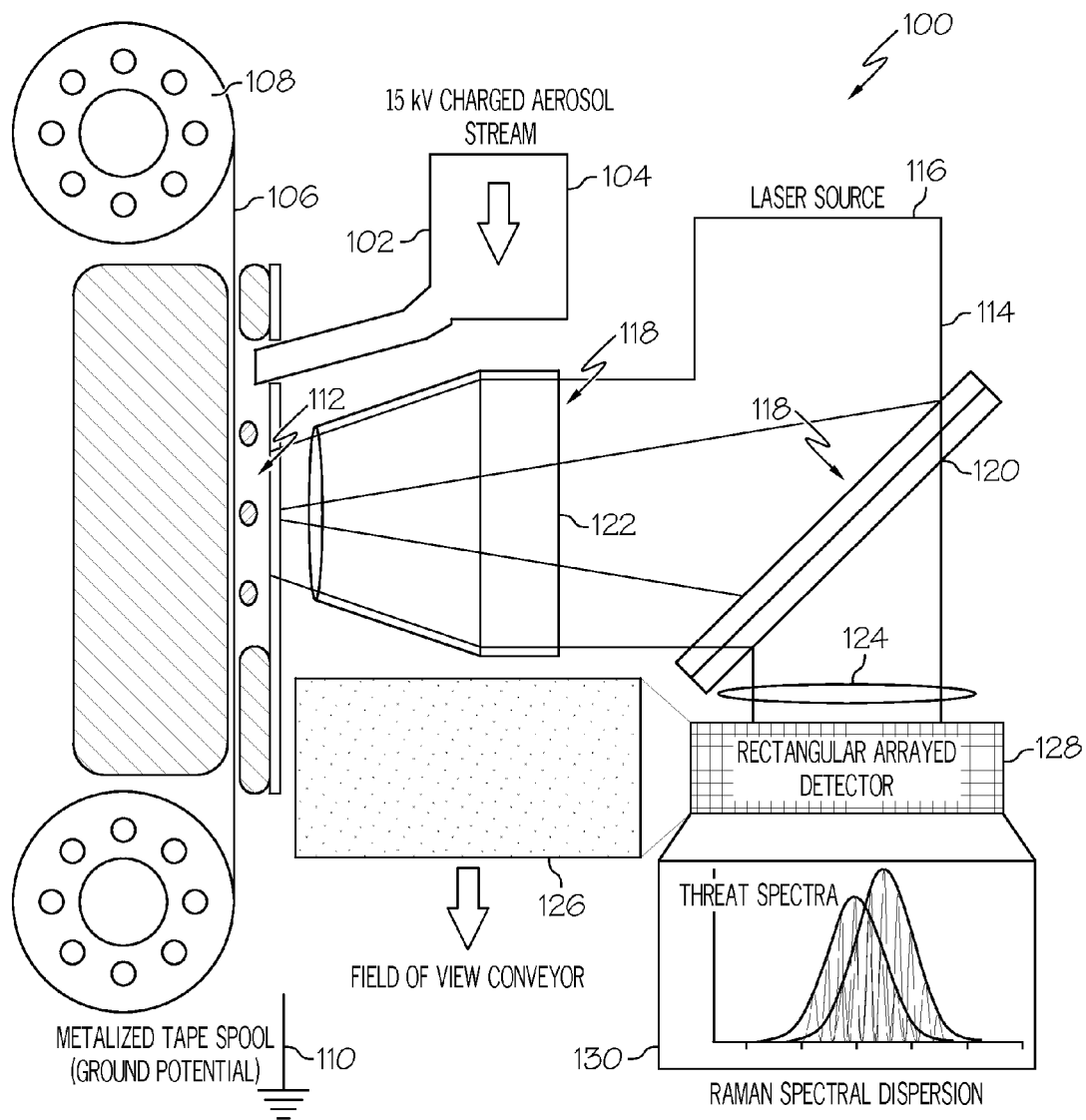
FIG. 2 is a block diagram illustrating a system for targeting biological and chemical materials according to further aspects of the present invention.

Referring to FIG. 2, according to various aspects of the present invention, a device 100 is provided, which utilizes Raman scattering as a means to detect aerosol particles, such as biological particles and non-biological particles, without depending on fluorescence. The device 100 may be reagent free, and may provide rapid response. For example, accurate detection of particulates of interest may be performed within a measure of seconds. Moreover, the system 100 is flexible and sensitive, e.g., able to be tuned to detect different particle types.

According to various aspects of the present invention, the device 100 includes a sampler 102 to collect samples onto a sample substrate for interrogation. The illustrative sampler 102 may comprise, for example, a small area electrostatic aerosol collector that collects aerosol particles out of that air by charging particles that enter an air inlet 104. The particles are charged, e.g., using a high voltage power source, and the charged particles are then impacted on an oppositely charged (or neutral charged) impaction substrate 106. For example, near 100% collection efficiency may be realized by a small area electrostatic aerosol collector at the illustrative flow rate of 1 L min-1. However, other collection technologies and flow rates may alternatively be implemented.

The impaction substrate 106 may comprise, for example, an aluminized Mylar tape. For example, as illustrated, the impaction substrate 106 is wound around a metalized tape spool 108, which is configured such that the surface of the impaction substrate 106 that collects the particulates is held at a ground potential 110.

The impaction substrate 106, e.g., the tape, may be in constant motion, e.g., at a speed of tens of μm per second, so that after impaction the aerosol particles that are collected by the sampler 102 are moved towards an interrogation region 112. Alternatively, the impaction substrate 106 may be jogged or otherwise advanced, as the application dictates.

A detection system 114 is positioned proximate to the interrogation region 112 for evaluating collected particulates. The detection system 114 comprises in general, a laser source 116 and an optical system 118 comprising optical devices, e.g., a dichroic mirror 120, an objective 122, and a filter 124. However, in practice, the optical system 118 may comprise other and/or additional lenses, filters, mirrors, and other optical devices etc. For example, the detection system 114 may comprise the optical imaging system 10 described in greater detail above, with reference to FIG. 1.

According to various aspects of the present invention, the collected particles in the interrogation region 112, e.g., all of the collected particles, are illuminated by the laser source 116 such as a visible laser. For example, within the optical system 118, the laser beam is directed by the dichroic mirror 120 through the objective 122 positioned proximate to the interrogation region 112. The interaction between the laser light and the particles leads to Raman scattering of light that is shifted in wavelength from the laser 116. Light from the interrogation region 112 is collected, e.g., directed back through the objective 122 of the optical system. Moreover, light from the interrogation region 112 is scattered and dispersed in order to separate the wavelengths of the laser light reflected back into the system using appropriate filter optics 124.

In order to achieve rapid and sensitive detection, only one or a few selected wavelengths may be monitored. In this regard, wavelengths may be chosen for monitoring that have been shown to be sufficient to efficiently discriminate biological from non biological particles. Optimum wavelength bands may be definable which can be monitored in order to detect agents of interest.

Figure 3:
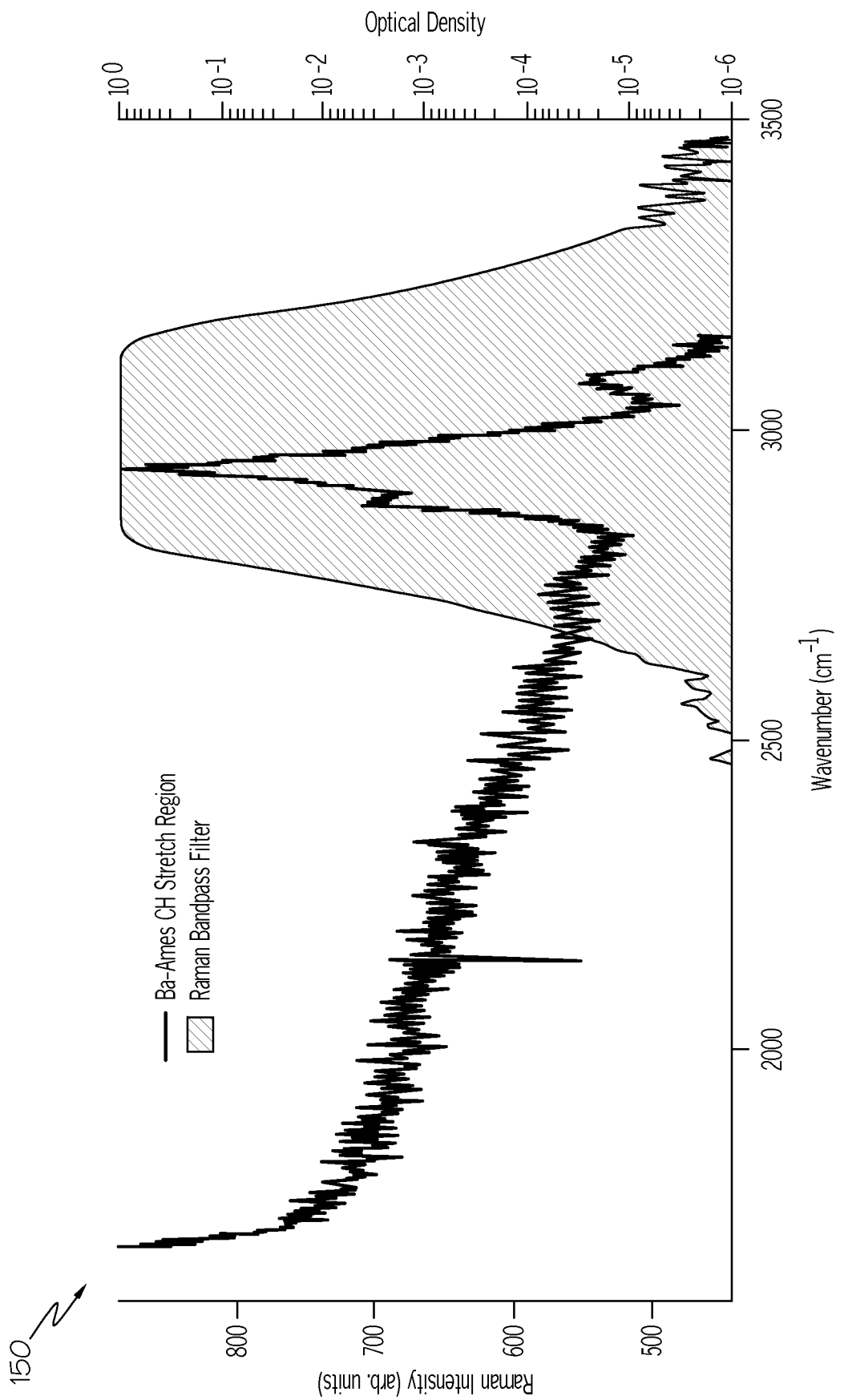
FIG. 3 is a chart illustrating Raman Intensity vs. Wavenumber vs. Optical density for an exemplary implementation according to various aspects of the present invention.

According to various aspects of the present invention the device 100 may be utilized for rapidly discriminating between biological and non-biological aerosol particles using narrow band Raman scattering. A typical biological particle Raman spectrum that may be detected by the device 100 is illustrated with reference to FIG. 3. With brief reference to FIG. 3, the large peak near 3000 $cm^{-1}$ Raman shift is due to the presence of carbon hydrogen (CH) bonds within the biological material in the illustrative example.

Referring back to FIG. 2, according to various aspects of the present invention, for purposes of illustration, and not by way of limitation, simulants as well as chemical aerosols were illuminated within an 80 $\mu m^2$ area or 80 μm long lines with 30 milliwatts (mW) of 633.2 nm laser light or less. This is schematically illustrated by the particles on the "field of view" conveyer 126. The Raman scattered light was filtered through the filter 124, e.g., a bandpass filter, illustrated as the gray region under the curve of FIG. 3, so that only CH scattered light was detected an output device 128 (detector), e.g., a cooled charge coupled device (CCD). With only three seconds of integration time, individual biological particles could be identified in the CCD image, which is illustrated schematically by the plot 130, which shows an exemplary "threat spectra" as a function of Raman spectral dispersion, while non biological particles did not appear in the illustrative image.

According to various aspects of the present invention, the basic approach described more fully herein may be possibly changed so as to make detection potentially more rapid, sensitive, and/or accurate. For example, depending upon the application, the specific laser 12, 116 and/or laser wavelength and/or laser power selected for interrogation may be different from that described above. Moreover, multiple types of output devices (detectors 16, 128) may be utilized in order to find options that will be sufficiently sensitive and low noise while being less expensive than cooled CCD arrays. Still further, the optical system 14, 116 may be modified with regard to the optics that collect the scattering from all of the particles in the illuminated field or illumination line and focuses their scattering onto the detector in order to provided the desired sensitivity according to the intended application. For example, it may be necessary to accurately detect the target particles by detecting wider spectral bands that could possibly distinguish fluorescence light from Raman scattered light.

According to various aspects of the present invention, the devices described more fully herein may be able to detect non fluorescent aerosol particles. The technology may even have a response time of less than five seconds because only a few seconds may be required to collect the particles on the tape substrate and move the particles into the interrogation region. Moreover, less than one second of interrogation may be sufficient to detect the Raman scattering. According to various aspects of the present invention, the technology may be able to detect the presence of a single target particle on the tape or other sample area. Moreover, the system 10, 100 may be able to discriminate the target, and possibly several targets, from background material. Because all potential targets have a unique Raman scattering signature, the various aspects of the present invention may be flexible and adaptable to different targets. Still further, according to various aspects of the present invention, the technology may not require the use of any reagents and may be able to operate continuously.

According to various aspects of the present invention, biological particles may be discriminated from non biological particles. Depending on the chemical aerosol agents of interest, it may be possible to implement a detector for several different agents. Doing so will require consideration of the optical system to efficiently collect light scattered at several different wavelengths.

Having thus described the invention of the present application in detail and by reference to embodiments thereof, it will be apparent that modifications and variations are possible without departing from the scope of the invention defined in the appended claims.

What is claimed is:

1. A biological and chemical microscopic targeting system, comprising:
    a light source configured to emit a laser beam;
    an imaging system configured to direct the beam towards a sample substrate along at least one optical path such that beam divergence causes the laser spot to be defocused with respect to an optical focal plane of the imaging system, the imaging system comprising an objective lens wherein:
        the beam passes through the objective lens to illuminate the sample substrate; and
        light collected from the sample substrate is directed back through the objective lens;
    optics that separate inelastically scattered photons from elastic incident photons comprising at least one filter defining a bandpass having a narrow bandwidth that filters the scattered photons to pass spectrally shifted wavelengths due to material on the sample substrate whose $C-H_x$ molecular bonds inelastically shift the wavelength of the incident photons and to attenuate inelastically scattered photons outside the narrow bandwidth; and
    an output device that discriminates between biological and chemical particles of interest from other particles contained on the sample substrate based upon detection solely within the narrow bandwidth, to a user.

2. The system according to claim 1, wherein the imaging system comprises a Galilean telescope that expands the beam in at least one dimension, wherein the beam is subsequently refocused in at least one dimension by a lens with a focal length approximately equal to the distance between the lens and a back aperture of a microscope objective.

3. The system according to claim 1, wherein the light source is configured to illuminate a sample area on the sample substrate in at least an 80 micron$^2$ field of view with at least 35 milliwatts of laser radiation having a wavelength less than 633 nm.

4. The system according to claim 3, wherein the optics that separate inelastically scattered photons from elastic incident photons comprises a long pass 633 nm dichroic mirror, and the at least one filter comprises a 633 nm long pass filter and 780 nm bandpass filter.

5. The system according to claim 4, wherein the dichroic mirror and long pass filter attenuates the fundamental wavelength of the laser at least one order of magnitude through the spectral range that is approximately between at least 500 nm through 633 nm.

6. The system according to claim 1, wherein the light source is configured to illuminate a sample area on the sample substrate in at least an 80 micron long line with less than 35 milliwatts of laser radiation having a wavelength between 576 nm and 650 nm.

7. The system according to claim 6, wherein the optics that separate inelastically scattered photons from elastic incident photons comprises a long pass dichroic mirror, and the at least one filter comprises a long pass filter and bandpass filter 3000 cm$^{-1}$ less than the laser wavelength.

8. The system according to claim 1, wherein the output device comprises a charge coupled device camera that relates the spatial location of a sample material on the sample substrate that reflects $C-H_x$ inelastic scattering information.

9. The system according to claim 1, wherein results from the output device are utilized in combination with at least one of visible image spatial information and fluorescence spatial information to increase the probability of the material being biological or organic in nature.

10. The system according to claim 1, wherein results from the output device are utilized in combination with the detection of at least one other type of molecular bonding detected in the sample on the sample substrate to increase the probability of detecting materials of interest.

11. The system according to claim 1, further comprising at least two filters, wherein two images are collected by the output device, one image collected using each filter, wherein the images are subtracted from one another to reveal the narrow bandwidth associated with the spectrally narrow region of the spectrum where $C-H_x$ inelastic scattering occurs.

12. The system according to claim 1, wherein the sample substrate comprises a tape based system that continuously moves a sample collected onto a tape substrate into an interrogation region of the imaging system.

13. A method of performing biological and chemical microscopic targeting, comprising:
    directing a laser beam from a light source towards a sample substrate along at least one optical path of an imaging system such that beam divergence causes the laser spot to be defocused with respect to an optical focal plane of the imaging system;
    passing the beam through an objective lens to illuminate the sample substrate;
    collecting light from the sample substrate that reflects back through the imaging system;
    separating inelastically scattered photons from elastic incident photons, where the inelastically scattered photons are bandpass filtered within a narrow bandwidth to pass spectrally shifted wavelengths due to material on the sample substrate whose $C-H_x$ molecular bonds inelastically shift the wavelength of the incident photons and to attenuate inelastically scattered photons outside the narrow bandwidth; and
    passing the filtered inelastically scattered photons to an output device to convey information that discriminates between biological and chemical particles of interest from other particles contained on the sample substrate based upon detection solely within the narrow bandwidth, to a user.

14. The method according to claim 13, wherein directing a laser beam from a light source towards a sample substrate along at least one optical path of an imaging system comprises passing the beam through a Galilean telescope that expands the beam in at least one dimension, wherein the beam is subsequently refocused in at least one dimension by a lens with a focal length approximately equal to the distance between the lens and a back aperture of a microscope objective.

15. The method according to claim 13, wherein directing a laser beam from a light source towards a sample substrate along at least one optical path of an imaging system comprises configuring the laser beam to illuminate a sample area on the sample substrate in at least an 80 micron$^2$ field of view with at least 35 milliwatts of laser radiation having a wavelength less than 633 nm.

16. The method according to claim 15, wherein separating inelastically scattered photons from elastic incident photons comprises directing elastically scattered photons using a long pass 633 nm dichroic mirror, and filtering the photons using a 633 nm long pass filter and 780 nm bandpass filter.

17. The method according to claim 16, further comprising using the dichroic mirror and long pass filter to attenuate the fundamental wavelength of the laser at least one order of magnitude through the spectral range that is approximately between at least 500 nm through 633 nm.

18. The method according to claim 13, wherein passing the inelastically scattered photons to an output device comprises passing the inelastically scattered photons to a charge coupled device camera that relates the spatial location of the material in the sample plane that reflects C—H$_x$ inelastic scattering information.

19. The method according to claim 13, further comprising utilizing the spatial C—H$_x$ inelastic scattering information in combination with at least one of visible image spatial information and fluorescence spatial information to increase the probability of the material being biological or organic in nature.

20. The method according to claim 13, further comprising utilizing the spatial C—H$_x$ inelastic scattering information in combination with the detection of at least one other type of molecular bonding to increase the probability of spatially detecting materials of interest.

21. The method according to claim 13, further comprising utilizing at least two filters to filter the light collected from the sample substrate, wherein two images are collected by the output device, one image collected using each filter, wherein the images are subtracted from one another to reveal the narrow bandwidth associated with the spectrally narrow region of the spectrum where C—H$_x$ inelastic scattering occurs.

22. The method according to claim 13, further comprising:
using a tape as the sample substrate; and
moving a sample collected onto a tape substrate into an interrogation region of the imaging system.

* * * * *